(12) United States Patent
Thomas et al.

(10) Patent No.: US 10,130,470 B2
(45) Date of Patent: Nov. 20, 2018

(54) SLEEVE FOR FACILITATING MOVEMENT OF A TRANSFEMORAL CATHETER

(75) Inventors: Ralph Joseph Thomas, Champlin, MN (US); Huisun Wang, Maple Grove, MN (US); Jacob John Daly, Blaine, MN (US); Thomas A. Savard, Arden Hills, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 505 days.

(21) Appl. No.: 13/817,056

(22) PCT Filed: Aug. 17, 2011

(86) PCT No.: PCT/US2011/001446
§ 371 (c)(1),
(2), (4) Date: Sep. 17, 2013

(87) PCT Pub. No.: WO2012/023980
PCT Pub. Date: Feb. 23, 2012

(65) Prior Publication Data
US 2014/0005768 A1 Jan. 2, 2014

Related U.S. Application Data

(60) Provisional application No. 61/374,409, filed on Aug. 17, 2010.

(51) Int. Cl.
*A61F 2/24* (2006.01)
*A61M 25/01* (2006.01)
(Continued)

(52) U.S. Cl.
CPC .......... *A61F 2/2427* (2013.01); *A61F 2/2436* (2013.01); *A61M 25/0136* (2013.01);
(Continued)

(58) Field of Classification Search
CPC ................. A61F 2/95–2/97; A61F 2/24; A61F 2/2427–2/2439; A61M 25/01;
(Continued)

(56) References Cited

U.S. PATENT DOCUMENTS

| 4,423,730 A | 1/1984 | Gabbay |
| 4,471,777 A | 9/1984 | McCorkle, Jr. |

(Continued)

FOREIGN PATENT DOCUMENTS

| DE | 102004062296 A1 | 7/2006 |
| EP | 1129744 A1 | 9/2001 |

(Continued)

OTHER PUBLICATIONS

International Search Report dated Feb. 2, 2012 for Application No. PCT/US2011/001446.

(Continued)

*Primary Examiner* — Darwin Erezo
*Assistant Examiner* — Jonathan Hollm
(74) *Attorney, Agent, or Firm* — Lerner, David, Littenberg, Krumholz & Mentlik, LLP

(57) ABSTRACT

A delivery device (10) for an implantable medical device includes an inner shaft (26) extending in a longitudinal direction and defining a compartment (23) adapted to receive the medical device in an assembled condition, an outer shaft (22) surrounding a longitudinal portion of the inner shaft, and a distal sheath (24) operatively attached to the outer shaft (22). The distal sheath (24) is slidable between a first position enclosing the compartment (23) and a second position exposing the compartment (23) for deployment of the medical device. A sleeve 30 surrounds at least a longitudinal portion of the outer shaft (22) and provides a substantially blood tight bearing surface that facilitates sliding movement of the delivery device (10) in an introducer (2).

23 Claims, 5 Drawing Sheets

(51) Int. Cl.
*A61M 25/06* (2006.01)
*A61F 2/966* (2013.01)
*A61M 25/00* (2006.01)

(52) U.S. Cl.
CPC ......... *A61M 25/0668* (2013.01); *A61F 2/966* (2013.01); *A61M 25/0054* (2013.01); *A61M 25/0147* (2013.01); *A61M 2025/0175* (2013.01)

(58) Field of Classification Search
CPC .......... A61M 25/0105; A61M 25/0133; A61M 25/0141–25/0147; A61M 25/0152; A61M 2025/015; A61M 2025/0161; A61M 2025/0175–2025/0177; A61M 2025/0188
USPC ......... 623/1.11–1.13, 1.24, 2.11; 606/1, 108, 606/191–200; 604/528; 600/146–150
See application file for complete search history.

(56) References Cited

U.S. PATENT DOCUMENTS

| | | | |
|---|---|---|---|
| 4,546,759 A | 10/1985 | Solar | |
| 4,575,371 A | 3/1986 | Nordqvist et al. | |
| 5,090,958 A | 2/1992 | Sahota | |
| 5,120,299 A * | 6/1992 | Lombardi ........................ 600/18 | |
| 5,201,901 A * | 4/1993 | Harada ..................... A61F 2/88 | |
| | | | 604/104 |
| 5,334,160 A * | 8/1994 | Ellis ................... A61M 25/013 | |
| | | | 600/434 |
| 5,411,552 A * | 5/1995 | Andersen et al. ........... 623/2.18 | |
| 5,733,325 A | 3/1998 | Robinson et al. | |
| 5,795,325 A | 8/1998 | Valley et al. | |
| 5,797,952 A | 8/1998 | Klein | |
| 5,827,324 A | 10/1998 | Cassell et al. | |
| 5,868,706 A | 2/1999 | Cox | |
| 5,868,755 A * | 2/1999 | Kanner ................... A61F 2/958 | |
| | | | 606/108 |
| 5,924,424 A | 7/1999 | Stevens et al. | |
| 5,968,068 A | 10/1999 | Dehdashtian et al. | |
| 6,077,295 A | 6/2000 | Limon et al. | |
| 6,190,357 B1 | 2/2001 | Ferrari et al. | |
| 6,214,036 B1 | 4/2001 | Letendre et al. | |
| 6,231,588 B1 | 5/2001 | Zadno-Azizi | |
| 6,306,141 B1 | 10/2001 | Jervis | |
| 6,312,407 B1 | 11/2001 | Zadno-Azizi et al. | |
| 6,361,545 B1 | 3/2002 | Macoviak et al. | |
| 6,375,668 B1 | 4/2002 | Gifford et al. | |
| 6,482,228 B1 * | 11/2002 | Norred ........................ 623/2.17 | |
| 6,607,551 B1 | 8/2003 | Sullivan et al. | |
| 6,623,518 B2 | 9/2003 | Thompson et al. | |
| 6,776,791 B1 | 8/2004 | Stallings et al. | |
| 8,414,644 B2 | 4/2013 | Quadri et al. | |
| 8,608,792 B2 | 12/2013 | Silveira et al. | |
| 2002/0120323 A1 | 8/2002 | Thompson et al. | |
| 2003/0014007 A1 | 1/2003 | Eidenschink et al. | |
| 2003/0023265 A1 | 1/2003 | Forber | |
| 2003/0199963 A1* | 10/2003 | Tower ................... A61F 2/2433 | |
| | | | 623/1.11 |
| 2004/0087900 A1 | 5/2004 | Thompson et al. | |
| 2004/0093063 A1 | 5/2004 | Wright et al. | |
| 2004/0204749 A1 | 10/2004 | Gunderson | |
| 2004/0236406 A1 | 11/2004 | Gregorich | |
| 2004/0267346 A1 | 12/2004 | Shelso | |
| 2004/0267348 A1 | 12/2004 | Gunderson et al. | |
| 2005/0020974 A1* | 1/2005 | Noriega et al. ............ 604/95.04 | |
| 2005/0027345 A1* | 2/2005 | Horan ..................... A61F 2/013 | |
| | | | 623/1.12 |
| 2005/0033398 A1* | 2/2005 | Seguin ........................ 623/1.11 | |
| 2005/0049667 A1 | 3/2005 | Arbefeuille et al. | |
| 2005/0049674 A1 | 3/2005 | Berra et al. | |
| 2005/0065590 A1* | 3/2005 | Shelso ..................... A61F 2/966 | |
| | | | 623/1.11 |
| 2005/0090890 A1* | 4/2005 | Wu .......................... A61F 2/95 | |
| | | | 623/1.11 |
| 2005/0222662 A1 | 10/2005 | Thompson et al. | |
| 2006/0058865 A1 | 3/2006 | Case et al. | |
| 2006/0100688 A1 | 5/2006 | Jordan et al. | |
| 2006/0106415 A1 | 5/2006 | Gabbay | |
| 2006/0111771 A1 | 5/2006 | Ton et al. | |
| 2006/0142848 A1 | 6/2006 | Gabbay | |
| 2006/0149294 A1* | 7/2006 | Argentine ......... A61M 39/0606 | |
| | | | 606/108 |
| 2006/0167468 A1 | 7/2006 | Gabbay | |
| 2006/0195184 A1 | 8/2006 | Lane et al. | |
| 2006/0259120 A1 | 11/2006 | Vongphakdy et al. | |
| 2006/0276872 A1 | 12/2006 | Arbefeuille et al. | |
| 2007/0027534 A1 | 2/2007 | Bergheim et al. | |
| 2007/0073391 A1 | 3/2007 | Bourang et al. | |
| 2007/0088431 A1 | 4/2007 | Bourang et al. | |
| 2007/0106364 A1 | 5/2007 | Buzzard et al. | |
| 2007/0112422 A1 | 5/2007 | Dehdashtian | |
| 2007/0142858 A1 | 6/2007 | Bates | |
| 2007/0162100 A1 | 7/2007 | Gabbay | |
| 2007/0168013 A1 | 7/2007 | Douglas | |
| 2007/0203561 A1 | 8/2007 | Forster et al. | |
| 2007/0203575 A1 | 8/2007 | Forster et al. | |
| 2007/0233224 A1 | 10/2007 | Leynov et al. | |
| 2007/0239271 A1 | 10/2007 | Nguyen | |
| 2007/0293930 A1 | 12/2007 | Wang et al. | |
| 2008/0103443 A1 | 5/2008 | Kabrick et al. | |
| 2008/0114443 A1 | 5/2008 | Mitchell et al. | |
| 2008/0147182 A1 | 6/2008 | Righini et al. | |
| 2008/0221666 A1 | 9/2008 | Licata et al. | |
| 2008/0228255 A1 | 9/2008 | Rust et al. | |
| 2008/0255662 A1 | 10/2008 | Stacchino et al. | |
| 2008/0262590 A1 | 10/2008 | Murray | |
| 2008/0319526 A1 | 12/2008 | Hill et al. | |
| 2009/0054975 A1 | 2/2009 | del Nido et al. | |
| 2009/0143851 A1 | 6/2009 | Paul, Jr. | |
| 2009/0204197 A1* | 8/2009 | Dorn et al. .................. 623/1.11 | |
| 2009/0222035 A1 | 9/2009 | Schneiderman | |
| 2009/0228093 A1 | 9/2009 | Taylor et al. | |
| 2009/0276272 A1 | 11/2009 | Glynn | |
| 2009/0281610 A1 | 11/2009 | Parker | |
| 2009/0287290 A1 | 11/2009 | Macaulay et al. | |
| 2010/0070015 A1 | 3/2010 | Schneider et al. | |
| 2010/0131039 A1 | 5/2010 | Chau et al. | |
| 2010/0145438 A1 | 6/2010 | Barone | |
| 2010/0152834 A1 | 6/2010 | Hannes et al. | |
| 2010/0268315 A1 | 10/2010 | Glynn et al. | |
| 2010/0312325 A1* | 12/2010 | Dorn ..................... A61M 39/06 | |
| | | | 623/1.13 |
| 2011/0029065 A1 | 2/2011 | Wood et al. | |
| 2011/0077731 A1 | 3/2011 | Lee et al. | |
| 2011/0078350 A1 | 3/2011 | Carls | |
| 2011/0098805 A1* | 4/2011 | Dwork et al. ............... 623/2.11 | |
| 2011/0137401 A1 | 6/2011 | Dorn et al. | |
| 2011/0172764 A1 | 7/2011 | Badhwar | |
| 2011/0224678 A1 | 9/2011 | Gabbay | |
| 2011/0251665 A1 | 10/2011 | Schmitt et al. | |
| 2011/0251666 A1 | 10/2011 | Schmitt et al. | |
| 2011/0251679 A1* | 10/2011 | Wiemeyer et al. .......... 623/2.11 | |
| 2011/0257720 A1 | 10/2011 | Peterson et al. | |
| 2011/0264201 A1* | 10/2011 | Yeung et al. ................ 623/2.11 | |
| 2011/0264202 A1 | 10/2011 | Murray, III et al. | |
| 2011/0288636 A1 | 11/2011 | Rolando et al. | |
| 2011/0301685 A1 | 12/2011 | Kao | |
| 2012/0078350 A1 | 3/2012 | Wang et al. | |
| 2012/0123528 A1 | 5/2012 | Knippel et al. | |
| 2013/0131775 A1 | 5/2013 | Hadley et al. | |
| 2013/0204344 A1 | 8/2013 | Tatalovich et al. | |
| 2013/0274860 A1 | 10/2013 | Argentine | |

FOREIGN PATENT DOCUMENTS

| | | |
|---|---|---|
| EP | 1157673 A2 | 11/2001 |
| WO | 9620025 A1 | 7/1996 |
| WO | 9748343 A1 | 12/1997 |
| WO | 990065418 A1 | 12/1999 |
| WO | 2006069704 A2 | 7/2006 |
| WO | 2006124549 A1 | 11/2006 |
| WO | 2007002863 A2 | 1/2007 |
| WO | 2007134290 A2 | 11/2007 |

(56) References Cited

FOREIGN PATENT DOCUMENTS

| | | | |
|---|---|---|---|
| WO | 2008031103 | A2 | 3/2008 |
| WO | 2008097556 | A1 | 8/2008 |
| WO | 2009062955 | A1 | 5/2009 |
| WO | 2009/091509 | A1 | 7/2009 |
| WO | 2009108942 | A1 | 9/2009 |
| WO | 2010005524 | A2 | 1/2010 |
| WO | 2010022138 | A2 | 2/2010 |
| WO | 10051025 | A1 | 5/2010 |
| WO | 10087975 | A1 | 8/2010 |
| WO | 2011025945 | A1 | 3/2011 |
| WO | 2012009006 | A1 | 1/2012 |
| WO | 2012036740 | A2 | 3/2012 |
| WO | 2012038550 | A1 | 3/2012 |

OTHER PUBLICATIONS

International Search Report and Written Opinion for Application No. PCT/US2013/048413 dated Dec. 4, 2013.
International Search Report and Written Opinion for Application No. PCT/US2013/047891 dated Dec. 4, 2013.
International Search Report and Written Opinion for Application No. PCt/US2011/001218 dated Nov. 11, 2011.
International Search Report and Written Opinion for Application No. PCT/US2012/047283 dated Oct. 30, 2012.
International Search Report for Application No. PCY/US2011/001596 dated May 8, 2012.
Japanese Office Action for Application No. 2013-519648 dated Jun. 30, 2015.

\* cited by examiner

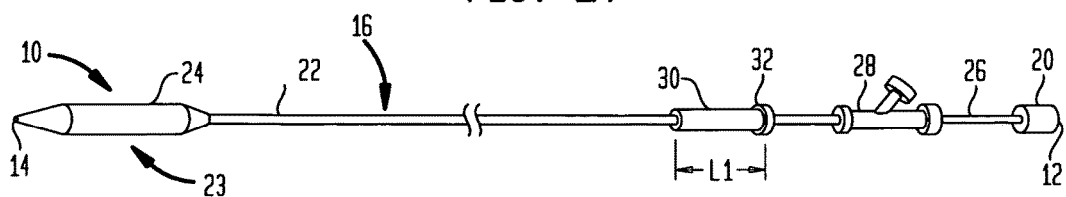
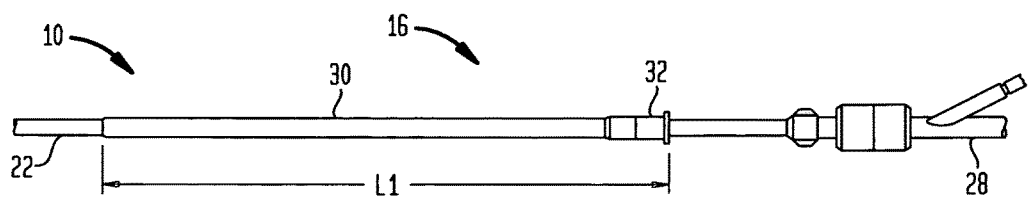
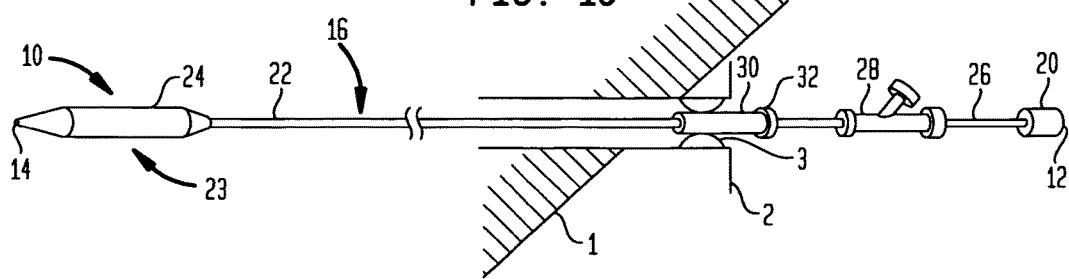

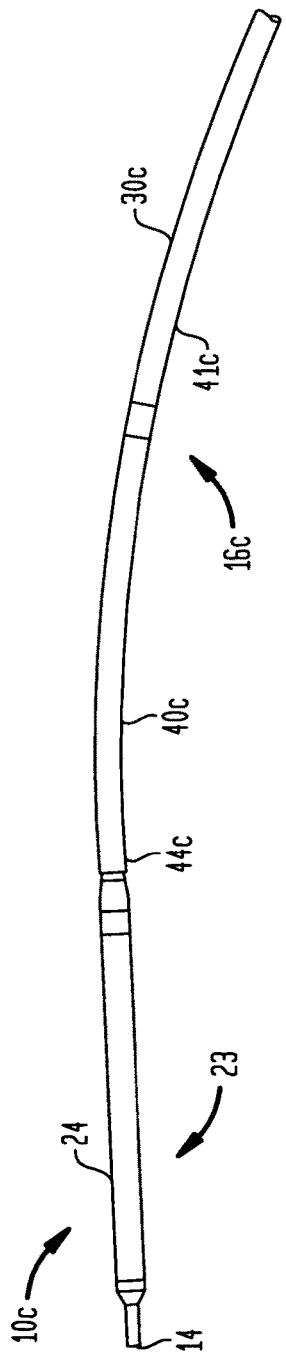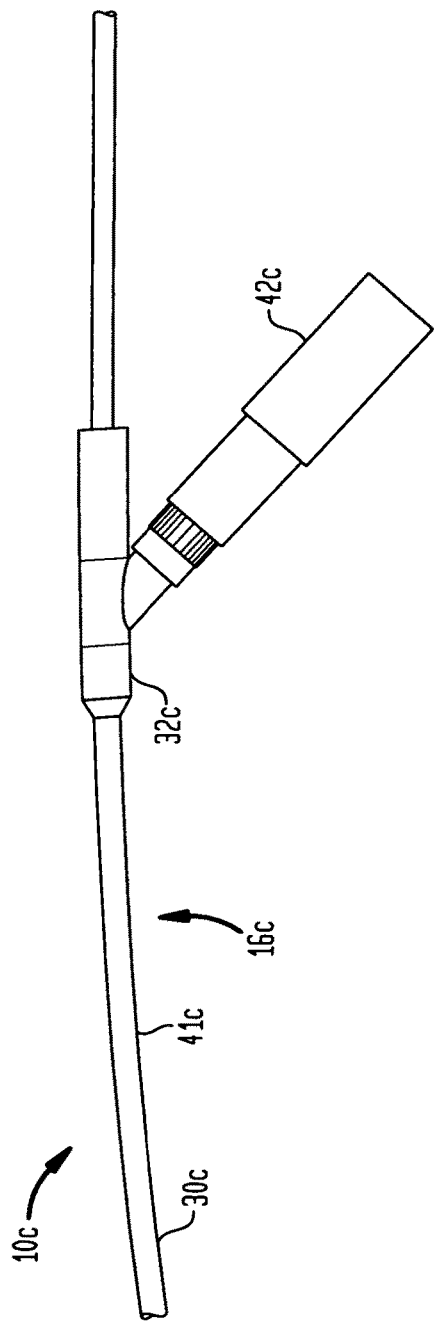

SLEEVE FOR FACILITATING MOVEMENT OF A TRANSFEMORAL CATHETER

CROSS-REFERENCE TO RELATED APPLICATIONS

This application is a national phase entry under 35 U.S.C. § 371 of International Application No. PCT/US2011/001446 filed Aug. 17, 2011, published in English, which claims the benefit of the filing date of U.S. Provisional Patent Application No. 61/374,409 filed Aug. 17, 2010, the disclosures of which are hereby incorporated herein by reference.

BACKGROUND OF THE INVENTION

The present invention is related to prosthetic heart valve replacement, and more particularly to devices, systems, and methods for reducing friction when using catheters and similar devices for transfemoral delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. To place such a valve into a delivery apparatus and ultimately into a patient, the valve must first be collapsed or crimped to reduce its circumferential size. For example, a conventional stent is typically collapsed and inserted into a distal sheath for delivery into a patient, for example, through a femoral artery.

When a collapsed prosthetic valve has reached the desired implant site in the patient (e.g., at or near the annulus of the patient's heart valve that is to be replaced by the prosthetic valve), the prosthetic valve can be released from the delivery apparatus and re-expanded to full operating size by unsheathing the stent containing the valve.

Despite the various improvements that have been made to the collapsible prosthetic heart valve delivery process, conventional delivery devices, systems, and methods suffer from some shortcomings.

In conventional transfemoral valve delivery devices, the distal sheath of the delivery device must have an inner diameter sufficiently large (e.g., a size of about 16 French) to cover a collapsed prosthetic heart valve, while the outer shaft of the delivery device that extends between the distal sheath and the handle must have a diameter sufficiently small (e.g., a size of about 12 French) to allow the outer shaft enough flexibility to bend around the aortic arch. When such a device is inserted into the femoral artery through an introducer, a hemostasis valve (e.g., a flat sheet of silicone rubber having a vertical slit and a horizontal slit) admits the distal sheath of the delivery device and seals around the outer shaft of the delivery device to prevent excessive bleeding.

A design tradeoff may exist because the hemostasis valve must be flexible enough to admit the larger distal sheath yet stiff enough to create a seal against the smaller outer shaft. If the hemostasis valve is too flexible, the seal against the outer shaft may be too weak, potentially resulting in excess bleeding. If the hemostasis valve is too stiff, the seal against the outer shaft may be too strong, potentially resulting in high operating friction when a user (e.g., a surgeon or an intervention cardiologist) needs to slide the outer shaft proximally within the hemostasis valve to deploy the heart valve.

If the force required to overcome a high amount of friction between the hemostasis valve and the outer shaft exceeds the force required to deploy the heart valve (i.e., the force required to overcome the friction between the stent portion of the valve and the distal sheath), the user may be forced to deploy the valve by pushing it out of the distal sheath towards the aortic annulus, rather than the preferred method of withdrawing the distal sheath from the heart valve while maintaining the position of the valve at the aortic annulus.

One potential solution to this design tradeoff could be to increase the diameter of the introducer and the hemostasis valve, but too large of an introducer (e.g., a size greater than about 20 French) may make it necessary to perform an additional surgical procedure to seal the entry point into the femoral artery.

Another potential solution to this design tradeoff could be to decrease the outer diameter of the distal sheath (e.g., to a size less than about 18 French), thereby allowing the use of an introducer and hemostasis valve having a smaller diameter. However, the distal sheath must accommodate a collapsible valve that is large enough to properly fit in the aortic annulus. Even in a collapsed state, a typical valve has a size of about 16 French, so a typical distal sheath must have an outer diameter size of at least about 18 French to accept a 16 French collapsed state implant, and a typical introducer must have an inner diameter sufficient to accept an 18 French outer diameter device.

There therefore is a need for further improvements to the devices, systems, and methods for transcatheter delivery of collapsible prosthetic heart valves. Among other advantages, the present invention may address one or more of these shortcomings.

BRIEF SUMMARY OF THE INVENTION

A delivery device for an implantable medical device, a system for implantable medical device delivery, and a method of delivering an implantable medical device are disclosed.

A delivery device for an implantable medical device includes an inner shaft extending in a longitudinal direction, the inner shaft defining a compartment adapted to receive the medical device in an assembled condition, an outer shaft surrounding at least a longitudinal portion of the inner shaft, the outer shaft being slidable relative to the inner shaft in the longitudinal direction, a distal sheath operatively attached to the outer shaft and surrounding a longitudinal portion of the inner shaft, the distal sheath having an outer diameter and being slidable in the longitudinal direction between a first position enclosing the compartment and a second position exposing the compartment for deployment of the medical device, and a sleeve surrounding at least a longitudinal portion of the outer shaft, the sleeve having an inner diameter less than the outer diameter of the distal sheath.

The sleeve and the outer shaft may define an average clearance therebetween of between about 0.001 inches and about 0.002 inches. The delivery device may further include a handle coupled to the inner and outer shafts and adapted to slide the outer shaft in the longitudinal direction relative to the inner shaft. The sleeve may be configured to be non-removable from the outer shaft. The sleeve may be splittable in the longitudinal direction for removal from the outer shaft. The sleeve may have an outer surface that tapers in the longitudinal direction from a relatively large proximal diameter to a relatively small distal diameter. The sleeve may include a distal steerable portion and a proximal portion, the steerable portion being more flexible than the proximal portion. The delivery device may further include a steering actuator coupled to the sleeve, wherein operation of the steering actuator bends the steerable portion of the sleeve. The delivery device may further include a pull-wire extending in the longitudinal direction from the steering actuator to a distal end of the steerable portion, whereby operation of the steering actuator causes the pull-wire to pull on the distal end of the steerable portion.

A system for implantable medical device delivery includes an introducer having an interior lumen and an introducer valve located in the interior lumen, and a delivery device including an inner shaft extending in a longitudinal direction, the inner shaft defining a compartment adapted to receive the medical device in an assembled condition, an outer shaft surrounding at least a longitudinal portion of the inner shaft, the outer shaft being slidable relative to the inner shaft in the longitudinal direction, a distal sheath operatively attached to the outer shaft and surrounding a longitudinal portion of the inner shaft, the distal sheath being slidable in the longitudinal direction between a first position enclosing the compartment and a second position exposing the compartment for deployment of the medical device, and a sleeve surrounding at least a longitudinal portion of the outer shaft, the delivery device being assembled in the introducer so that the sleeve is positioned in the interior lumen of the introducer and extends through the introducer valve.

The sleeve and the outer shaft may define an average clearance therebetween of between about 0.001 inches and about 0.002 inches. The delivery device may further include a handle coupled to the inner and outer shafts and adapted to slide the outer shaft in the longitudinal direction relative to the inner shaft. The sleeve may be configured to be non-removable from the outer shaft. The sleeve may be splittable in the longitudinal direction for removal from the outer shaft. The sleeve may have an outer surface that tapers in the longitudinal direction from a relatively large proximal diameter to a relatively small distal diameter. The sleeve may include a distal steerable portion and a proximal portion, the steerable portion being more flexible than the proximal portion. The delivery device may further include a steering actuator coupled to the sleeve, wherein operation of the steering actuator bends the steerable portion of the sleeve. The delivery device may further include a pull-wire extending in the longitudinal direction from the steering actuator to a distal end of the steerable portion, whereby operation of the steering actuator causes the pull-wire to pull on the distal end of the steerable portion.

A method of delivering an implantable medical device includes providing a delivery device including an inner shaft extending in a longitudinal direction, the inner shaft defining a compartment adapted to receive the medical device in an assembled condition, an outer shaft surrounding at least a longitudinal portion of the inner shaft, the outer shaft being slidable relative to the inner shaft in the longitudinal direction, a distal sheath operatively attached to the outer shaft and surrounding a longitudinal portion of the inner shaft, the distal sheath being slidable in the longitudinal direction between a first position enclosing the compartment and a second position exposing the compartment for deployment of the medical device, and a sleeve surrounding at least a longitudinal portion of the outer shaft, mounting the medical device in the compartment with the distal sheath in the first position, providing an introducer in a tract extending from an opening in a blood vessel of a patient and through tissue overlying the opening, the introducer having an interior lumen and an introducer valve located in the interior lumen, inserting the distal sheath of the delivery device into the patient through the introducer to position the medical device at a target location, positioning the sleeve in the introducer, the introducer valve creating a substantially leak-proof seal against an outer surface of the sleeve, advancing the distal sheath of the delivery device into the aortic arch of the patient, and deploying the medical device by withdrawing a proximal portion of the outer shaft out of the introducer, thereby sliding the distal sheath into the second position.

The medical device may be a prosthetic heart valve, and the target location may be the descending aorta. The method may further include removing the sleeve from the introducer by splitting it along a pre-determined longitudinal score and peeling the sleeve away from the outer shaft. The sleeve may include a distal steerable portion and a proximal portion, the steerable portion being more flexible than the proximal portion, and the delivery device may include a steering actuator coupled to the sleeve. The method may further include operating the steering actuator to bend the steerable portion of the sleeve. The delivery device may include a pull-wire extending in the longitudinal direction from the steering actuator to a distal end of the steerable portion. The method may further include operating the steering actuator to cause the pull-wire to pull on the distal end of the steerable portion, thereby bending the deflectable portion.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 1A is a diagrammatic side view of a transfemoral delivery device having a short sleeve;

FIG. 1B is an enlarged side view of a proximal portion of the delivery device depicted in FIG. 1A;

FIG. 1C is a diagrammatic side view of the delivery device depicted in FIG. 1A, shown inserted in an introducer;

FIG. 4A is a side view of a distal portion of a transfemoral delivery device having a long and actively deflectable sleeve; and FIG. 4B is a side view of a proximal portion of the delivery device depicted in FIG. 4A.

DETAILED DESCRIPTION

Figure 1D:
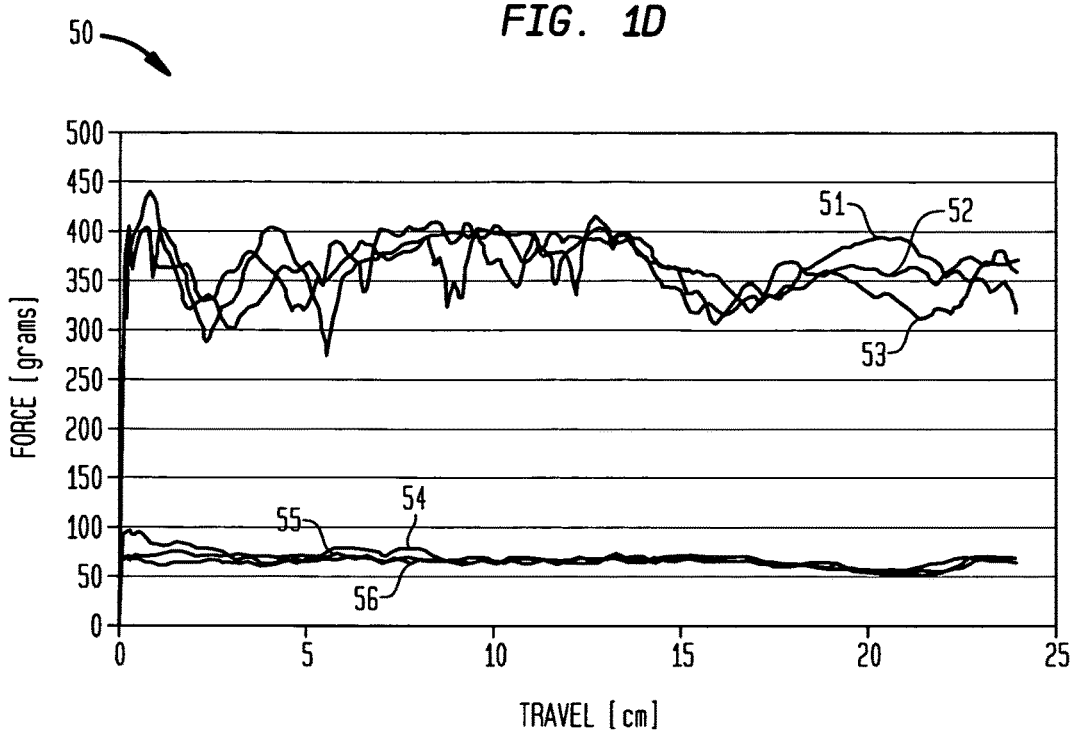
FIG. 1D is a graph of the catheter tracking force acting on the sleeve of the delivery device depicted in FIG. 1A compared to the catheter tracking force acting on a conventional delivery device.

Referring now to FIGS. 1A and 1B to illustrate the structure and function of the present invention, one embodiment of a delivery device 10 has a proximal end 12, a distal end 14, and a catheter assembly 16 extending from the proximal end 12 to the distal end 14. The delivery device 10 is an exemplary transfemoral delivery device for a collapsible prosthetic heart valve.

The catheter assembly 16 includes an inner shaft 26 extending from a hub 20 to the distal end 14, and an outer shaft 22 assembled over the inner shaft and slidable relative thereto. At the distal end of the outer shaft 22, the catheter assembly 16 includes a valve compartment 23 for securely holding a prosthetic heart valve in a collapsed condition around the inner shaft 26 for delivery into a patient. A distal sheath 24 encloses the valve compartment 23 and is connected to the distal end of the outer shaft 22 so that proximal movement of the outer shaft 22 relative to the compartment 23 moves the distal sheath 24 proximally to deploy the heart valve. At its proximal end, the outer shaft 22 includes a hemostasis valve 28. The hemostasis valve 28 preferably is a conventional hemostasis valve having an adjustable sealing member and a side port for flushing the space between the outer shaft 22 and the inner shaft 26, although in other example embodiments, any conventional hemostasis valve may be used. A sleeve 30 is slidably assembled over the outer shaft 22 distally of the hemostasis valve 28.

A handle (not shown) for controlling deployment of a collapsible heart valve located in the compartment 23 may be optionally coupled to the hemostasis valve 28 and the hub 20, such that the handle can provide a user more controlled maneuverability of the outer shaft 22 relative to the inner shaft 26. Such a handle may be included in any of the delivery device embodiments described herein. In embodiments not including a handle, a user (e.g., a surgeon or an intervention cardiologist) may slide the outer shaft 22 relative to the inner shaft 26 by gripping the hemostasis valve 28 and the hub 20 and sliding the hemostasis valve relative to the hub.

To load the delivery device 10 with a collapsible prosthetic valve, a user places the valve around the inner shaft 26 and compresses or crimps the valve until it fits inside the distal sheath 24, which holds the valve in a compressed state. When the valve is later unsheathed, the stent portion of the valve self-expands and disengages from the catheter assembly 16. The valve can also be resheathed before full deployment by sliding the distal sheath 24 back over the portion of the stent that has expanded, thereby recollapsing the expanded portion of the stent.

Referring now to FIG. 1C, the delivery device 10 is inserted through the skin 1 of a patient and into the patient's femoral artery through an introducer 2 located in a tract extending from an opening in the femoral artery and through tissue overlying the opening, the introducer having an interior lumen and an introducer valve 3 located in the interior lumen. The introducer valve 3 preferably is a hemostasis valve (e.g., a flat sheet of silicone rubber having a vertical slit and a horizontal slit). Alternatively, the introducer valve 3 may be a conventional sealing member suitable for use with an introducer, such as a rubber gasket having an o-ring or washer shape including a central aperture, or any other mechanism capable of providing a blood-tight seal between the introducer 2 and the sleeve 30 while allowing relative movement therebetween. Rather than having the introducer valve 3 directly contact the outer shaft 22 as in a conventional delivery device, the introducer valve contacts the outer surface of the sleeve 30, while the outer surface of the outer shaft 22 contacts the inner surface of the sleeve 30. The sleeve 30 includes a hub 32 having an outer diameter that is greater than the inner diameter of the introducer 2, so that the hub 32 can prevent the sleeve 30 from fully passing into the introducer 2 and getting past the introducer valve 3.

The sleeve 30 preferably is designed to minimize bleeding and to minimize the friction force that must be overcome to deploy the valve into a patient (i.e., to withdraw the distal sheath 24 from over the valve). Sleeve 30 may have any length, including lengths from about 1" to about 6", and preferably from about 1" to about 3". In the embodiment shown in FIG. 1B, the sleeve 30 has a length L1 that is about 6".

To minimize bleeding between the introducer 2 and the sleeve 30, the sleeve may be formed with an outer diameter that is slightly smaller than the inner diameter of the introducer 2, and the introducer valve 3 may close the gap therebetween. For example, a sleeve 30 (or any of the other sleeve embodiments disclosed herein) having an outer size of 18 French (0.236") may create a substantially leak-proof seal when used with an introducer 2 having an inner diameter (i.e., interior lumen) of 0.245" and an introducer valve 3 that closes the 0.009" gap therebetween. This may also be accomplished by making the outer diameter of the sleeve 30 greater than the diameter of the opening in the introducer valve 3, producing an interference fit between the sleeve 30 and the introducer valve 3.

To minimize bleeding between the outer shaft 22 and the sleeve 30, the sleeve may be formed with an inner diameter that is closely matched with the outer diameter of the outer shaft 22, such that the gap therebetween is sufficiently small to prevent significant flow of blood into the gap (e.g., the surface tension of the blood may prevent the blood from flowing into a very small gap). For example, a sleeve 30 (or any of the other sleeve embodiments disclosed herein) with an inner diameter of about 0.160" (equivalent to slightly larger than 12 French) and an outer shaft 22 with an outer diameter of about 0.158" (equivalent to 12 French) together will produce an average clearance of about 0.001" between the sleeve 30 and the outer shaft 22. It is believed that an average clearance between the sleeve 30 and the outer shaft 22 of up to about 0.002" will be sufficiently small to prevent significant blood flow therebetween. Accordingly, average clearances of between about 0.001" and about 0.002" are preferred. An average clearance between the sleeve 30 and the outer shaft 22 of greater than about 0.002" may also be sufficiently small to prevent significant blood flow therebetween, but the required clearance may depend on the length of the sleeve (i.e., a longer sleeve may 30 permit a greater clearance between the sleeve and the outer shaft 22 while still preventing significant blood flow therebetween).

It will be appreciated from the foregoing that the inner diameter of the sleeve 30 will be much less than the diameter of the distal sheath 24. Accordingly, the distal sheath 24 cannot be passed through sleeve 30 during insertion of the delivery device 10 in a patient. Rather, the sleeve 30 must be pre-assembled to the delivery device 10, either when the delivery device is manufactured or at any other time prior to insertion of the delivery device into a patient.

To minimize the friction force acting on the outer shaft 22 during deployment of the valve, there preferably is a relatively low amount of friction between the outer shaft 22 and the sleeve 30. This may be accomplished by making the sleeve 30 from a different material than the outer shaft 22, and in particular, by using a material for the sleeve 30 that produces low friction when it is slid against a conventional outer shaft 22. For example, the sleeve 30 preferably is made of a polymer material such as PTFE, PEEK, braided polyether block amide (Pebax®), or any other biocompatible material that produces relatively low friction when slid against a conventional outer shaft 22 made, for example, from nylon.

Rather than making the entirety of the sleeve 30 from a different material than the outer shaft 22, only the portion of the sleeve 30 that contacts the outer shaft need be made from a different material. In embodiments where the sleeve 30 and the outer shaft 22 are both made substantially of the same material, such as nylon or polyether block amide) (Pebax®, the sleeve may include a thin liner (e.g., about 0.001" thick) made, for example, from PTFE, and attached to the interior surface of the sleeve. In such embodiments, the outer shaft 22 can slide without binding against the PTFE liner during use.

To minimize the need to surgically seal the femoral artery after the introducer 2 has been removed, the outer diameter of the sleeve 30 (or any of the other sleeve embodiments disclosed herein) preferably is as small as possible, and more preferably is equal to or less than the outer diameter of the distal sheath 24. Because both the distal sheath 24 and the sleeve 30 must be inserted into the introducer 2, keeping the diameter of the sleeve 30 no greater than the diameter of the distal sheath 24 will help to minimize the diameter of the introducer 2.

Referring now to FIG. 1D, graph 50 is a comparison of catheter tracking force acting on the delivery device 10 having a sleeve 30, as depicted in FIG. 1A, with the catheter tracking force acting on a conventional delivery device that has no sleeve. As used herein, the tracking force acting on a delivery device is the amount of force required to advance the delivery device through the patient's vasculature, as recorded by a force gauge coupled to the proximal end of the device. Catheter tracking force is measured with the inner and outer shafts of the delivery device locked together such that relative movement therebetween is prevented. Because there is no relative movement of the inner and outer shafts during measurement of the tracking force (and thus, no deployment of a valve), the force measured is almost entirely due to the friction between the introducer valve and either the sleeve or the outer shaft. During the trials depicted in graph 50, a straight plastic shaft containing saline was used to simulate a vasculature containing blood, so a small amount of resistance may also have been generated between the saline and the catheter assembly.

Lines 51, 52, and 53 represent the catheter tracking force measured at the proximal end of a conventional delivery device (with no sleeve) as the outer shaft is advanced through the introducer valve and the simulated vasculature, over approximately a 24 cm travel distance. Lines 54, 55, and 56 represent the catheter tracking force measured at the proximal end of the delivery device 10 as the outer shaft 22 is advanced through the sleeve 30 and the simulated vasculature (with the sleeve 30 positioned inside of the introducer valve), over approximately a 24 cm travel distance.

As can be seen in FIG. 1D, the tracking force measured for the delivery device 10 (using the sleeve 30) is between 50 and 100 grams throughout the travel distance. In contrast, the tracking force measured for the conventional delivery device (without using a sleeve) is generally between 300 and 450 grams throughout the travel distance. Hence, the delivery device 10 employing the sleeve 30 experiences approximately 80% less tracking force than the conventional delivery device without a sleeve. In an example wherein the force required to unsheathe a 2" long self-expanding heart valve is approximately 1000 grams, the delivery device 10 may experience a total heart valve deployment force of 1050-1100 grams (tracking force plus unsheathing force), whereas a conventional delivery device may experience a total heart valve deployment force of 1300-1450 grams. Therefore, the delivery device 10 may require approximately 22% less heart valve deployment force than the conventional delivery device.

Figure 1E:
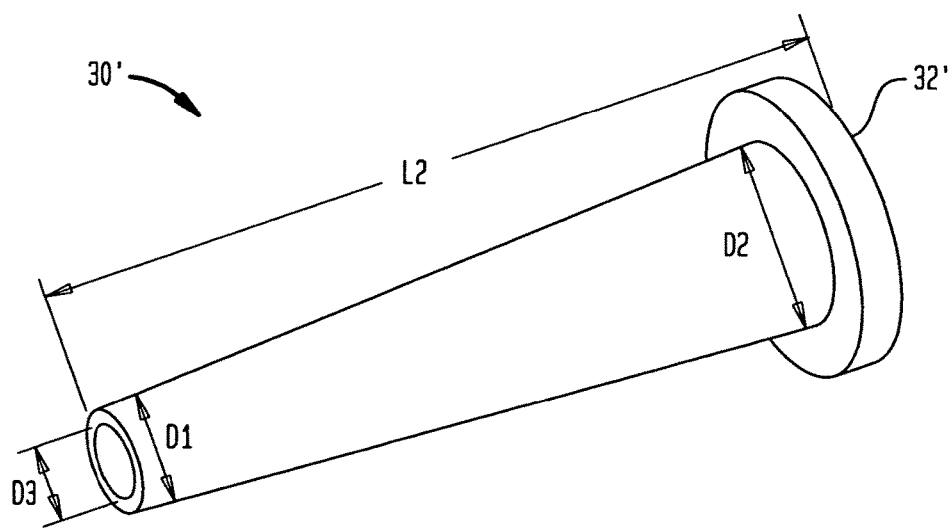
FIG. 1E is a perspective view of a short sleeve with a tapered outer diameter suitable for use in the device of FIG. 1A.

Referring now to FIG. 1E, a sleeve 30' suitable for use in the device of FIG. 1A has a hub 32' and a tapered outer surface, such that the diameter D1 at the distal end of the sleeve is less than the diameter D2 at the proximal end of the sleeve. Such a tapered outer surface may allow the sleeve 30' to produce an increasingly tighter fit against the introducer valve 3 as the sleeve is inserted into the introducer 2, thereby ensuring achievement of a sufficiently snug fit between the sleeve and the introducer valve to minimize bleeding.

The sleeve 30' has an inner diameter D3 that remains substantially constant along the longitudinal length L2 of the sleeve, so that the preferred average clearance between the inner surface of the sleeve and the outer surface of the outer shaft 22 (e.g., about 0.001" to about 0.002") is substantially maintained along the length L2 of the sleeve.

Figure 2A:
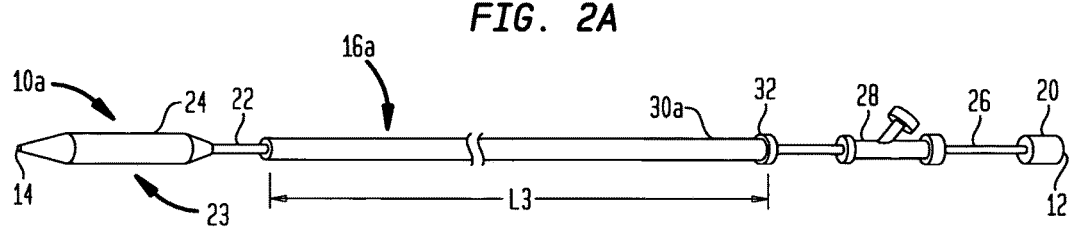
FIG. 2A is a diagrammatic side view of a transfemoral delivery device having a long sleeve.

Referring now to FIG. 2A, another embodiment of a delivery device 10a is shown. The delivery device 10a is substantially the same as the delivery device 10 shown in FIGS. 1A-1C, except it has a sleeve 30a that is longer than sleeves 30 or 30'. The delivery device 10a has a proximal end 12, a distal end 14, and a catheter assembly 16a extending from the proximal end 12 to the distal end 14.

The catheter assembly 16a includes an inner shaft 26 extending from a hub 20 to the distal end 14, and an outer shaft 22 assembled over the inner shaft so as to be slidable relative to same. At the distal end of the outer shaft 22, the catheter assembly 16a includes a valve compartment 23 for holding a prosthetic heart valve in a compressed condition around the inner shaft 26 for delivery into a patient. A distal sheath 24 enclosing the valve compartment 23 is connected to the distal end of the outer shaft 22 so as to be movable therewith. Hence, proximal movement of the outer shaft 22 moves the distal sheath 24 proximally relative to the compartment 23 so as to deploy the heart valve. At its proximal end, the outer shaft 22 includes a hemostasis valve 28. A sleeve 30a having a length L3 and a hub 32 at its proximal end is assembled slidably over the outer shaft 22 distally of the hemostasis valve 28. The sleeve 30a may have any length, but it preferably has a length L3 that is slightly shorter (e.g., about 2" shorter) than the length of the outer shaft 22. For example, the sleeve 30a preferably extends from a location close to the hemostasis valve 28 to a location close to the distal sheath 24, but sufficiently spaced from the distal sheath that the distal sheath 24 may be fully retracted off of the compartment 23 without contacting the sleeve 30a. For example, where a heart valve having a length of about 2" is positioned inside of the compartment 23, the sleeve 30a preferably has a length L3 that is about 2" shorter than the distance between the hemostasis valve 28 and the proximal end of the distal sheath 24, thereby allowing full deployment of the heart valve. In example embodiments, the sleeve 30a may have a length L3 between about 24" and about 42".

Figure 2B:
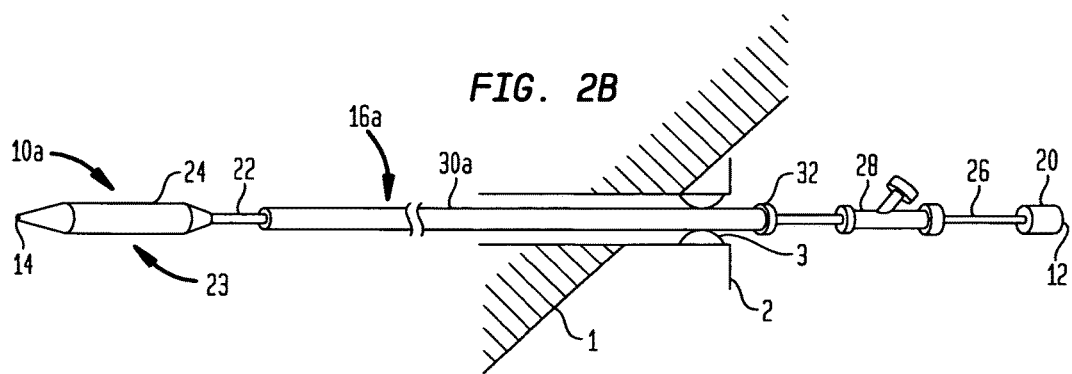
FIG. 2B is a diagrammatic side view of the delivery device depicted in FIG. 2A, shown inserted in an introducer.

Referring now to FIG. 2B, the delivery device 10a is inserted through the skin 1 of a patient and into the patient's femoral artery through an introducer 2 having an introducer valve 3. Similar to the delivery device 10 shown in FIGS. 1A-1C, the introducer valve 3 contacts the outer surface of the sleeve 30a, while the outer surface of the outer shaft 22 contacts the inner surface of the sleeve, preferably in such manner as to minimize bleeding and the friction force that must be overcome to deploy the heart valve.

Similar to the short sleeve 30, the long sleeve 30a (and all of the other sleeves disclosed herein) may include a thin liner (e.g., about 0.001" thick) made, for example, from PTFE, and attached to the interior surface of the sleeve. In such embodiments, the outer shaft 22 can slide without binding against the PTFE liner during use.

The long sleeve 30a (and any of the other long sleeve embodiments disclosed herein) may permit a greater clearance and/or variation in clearance between the sleeve and the outer shaft 22 than with the short sleeves 30 and 30', while still preventing significant blood flow therebetween. For example, although the clearance between the sleeve 30a and the outer shaft 22 may be greater than 0.002" along some or all of the length L3 of the sleeve, the greater distance the blood has to travel lessens the likelihood of excess bleeding than would be the case for the short sleeves 30 or 30' providing a similar clearance.

Both the short sleeve 30 and the long sleeve 30a (or any of the other sleeve embodiments disclosed herein) may be configured to be non-removable from their respective delivery devices 10 and 10a. In some embodiments (not shown), the short sleeve 30 or the long sleeve 30a may be configured to be split along a pre-determined score line and peeled away from the outer shaft 22 by a user after acceptable placement of the heart valve in the proper location in the patient.

In embodiments having a long sleeve, it is highly desirable for the delivery device to include a mechanism that enables the sleeve to steer the distal sheath through the aortic arch. In that regard, it is preferred that such delivery devices include a sheath that is steerable through operation by a user. One embodiment of such a delivery device including a steerable sheath is shown in FIG. 3A.

Figure 3A:
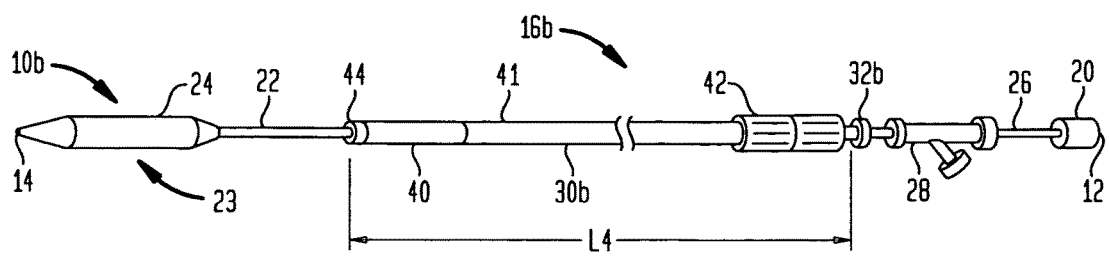
FIG. 3A is a diagrammatic side view of a transfemoral delivery device having a long and actively deflectable sleeve.

Referring now to FIG. 3A, another embodiment of a delivery device 10b having a long and steerable sleeve 30b is shown. The delivery device 10b is substantially the same as the delivery device 10a shown in FIGS. 2A and 2B, except that a distal portion of the sleeve 30b is steerable.

The delivery device 10b has a proximal end 12, a distal end 14, and a catheter assembly 16b extending from the proximal end 12 to the distal end 14. The catheter assembly 16b includes an inner shaft 26 extending from a hub 20 to the distal end 14, and an outer shaft 22 assembled over the inner shaft for sliding movement therebetween. At the distal end of the outer shaft 22, the catheter assembly 16b includes a valve compartment 23 for holding a prosthetic heart valve in a collapsed condition around the inner shaft 26 for delivery into a patient. A distal sheath 24 encloses the compartment 23 and is connected to the distal end of the outer shaft 22 so that sliding movement of the outer shaft 22 along the inner shaft 26 results in a corresponding movement of the distal sheath 24 relative to the compartment 23 for deployment of the heart valve. At its proximal end, the outer shaft 22 includes a hemostasis valve 28. A long and steerable sleeve 30b having a hub 32b at its proximal end is assembled slidably over the outer shaft 22 distally of the hemostasis valve 28. Similar to the sleeve 30a shown in FIGS. 2A and 2B, the sleeve 30b preferably has a length L4 that is about 2" shorter than the distance between the hemostasis valve 28 and the proximal end of the distal sheath 24, thereby allowing full deployment of a heart valve that is about 2" long. In example embodiments, the sleeve 30b may have a length L4 between about 24" and about 42".

Because the long sleeves 30a and 30b extend farther into the vasculature than the short sleeves 30 and 30', and because the long sleeves 30a and 30b have a greater diameter than the outer shaft 22, the long sleeves 30a and 30b may contract the vasculature over a higher surface area during advancement of the devices 10a and 10b than would the outer shaft 22 of the device 10 having a shorter sleeve. A higher contact surface area may produce a higher friction force during advancement of the devices 10a and 10b. Furthermore, the assembly of the sleeves 30a and 30b over the outer shaft 22 for a longer distance may cause the catheter assemblies 16a and 16b to be stiffer than the catheter assembly 16. Stiffer catheter assemblies may increase the risk of damaging the vasculature during advancement of the devices 10a and 10b due to a higher contact force between the distal tip 14 of the devices and the vasculature as the distal tip is advanced through the aortic arch.

The sleeve 30b includes a steerable portion 40 located near the distal end of the sleeve and a proximal portion 41, a steering actuator 42 located near the proximal end of the sleeve, a pull-ring (not shown) embedded in a distal end 44 of the steerable portion 40, and one or more pull-wires (not shown) extending longitudinally along a side wall of the sleeve and coupled at one end to the pull-ring and at the other end to a pull mechanism of the steering actuator 42. The steerable portion 40 may have any length, including for example, a length between about 1" and about 3". In preferred embodiments, however, the steerable portion 40 has a length of about 2". The inclusion of a steerable portion 40 in the long sleeve 30b may help reduce friction acting on the catheter assembly 16b and the contact force between the distal tip 14 and the vasculature during advancement of the device 10b through the vasculature.

The steerable portion 40 of the sleeve 30b that may bend around the aortic arch preferably is softer (and thus, more flexible) than the proximal portion 41 that may remain relatively straight during use of the delivery device 10b. The inclusion of a relatively soft material in the long sleeves 30a and 30b may help to make the sleeves more flexible, thereby minimizing any increase in the stiffness of the catheter assemblies 16a and 16b (compared to the catheter assembly 16) and the potential for damage during advancement through the vasculature. The long sleeves 30a and 30b preferably are made of a soft plastic material such as nylon, polyether block amide (Pebax®), or polyurethane. The steerable portion 40 of the sleeve 30b may have a hardness of about 40D to about 45D, while the proximal portion 41 may have a hardness of about 72D. The steerable portion 40 and the proximal portion 41 may be made from the same or different materials. If the steerable portion 40 and the proximal portion 41 are made from the same material, the steerable portion may be made more flexible by using different compounding parameters than the proximal portion.

Figure 3B:
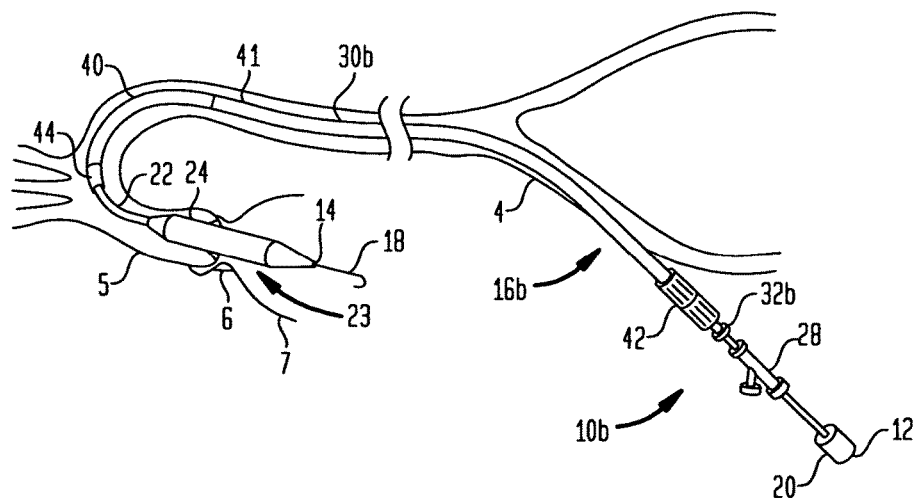
FIG. 3B is a diagrammatic side view of the delivery device depicted in FIG. 3A, shown inserted in a femoral artery and through an aortic arch.

As shown in FIGS. 3A and 3B, the steerable portion 40 is actively steerable, whereby a user can use the steering actuator 42 to actively maneuver the steerable portion 40 through the vasculature (e.g., through the aortic arch). In some embodiments (not shown), the steerable portion 40 may be passively steerable because it is sufficiently more flexible than the proximal portion 41, whereby the steering actuator 42, the pull-ring, and the pull wires may be omitted from the delivery device 10b. A steerable portion 40 that is either actively or passively steerable may be able to deflect or curve more easily than the proximal portion 41 as the sleeve 30b is advanced through the vasculature.

Making the proximal portion 41 stiffer than the steerable portion 40 (rather than having the entire sleeve 30b be as flexible as the steerable portion 40) may help to maintain a sufficient axial strength in the sleeve 30b to avoid kinking of the sleeve as it is advanced through the vasculature. Also, to help avoid such potential kinking, either or both of the steerable portion 40 and the proximal portion 41 may be reinforced by braided metal wires.

Referring now to FIG. 3B, the presence of the steerable portion 40 in the sleeve 30b may allow the catheter assembly 16b to more easily conform to the shape of the aortic arch 5 while the distal sheath 24 containing the heart valve is being advanced towards the aortic annulus 6.

In use, a user may insert the distal end 14 of the delivery device 10b into the femoral artery 4 of a patient to deliver a collapsible prosthetic valve to the aortic annulus 6. The user may advance the delivery device 10b over a guide wire 18 to guide the distal end 14 of the delivery device 10b through the femoral artery 4, the aortic arch 5, and the aortic annulus 6, and into the left ventricle of the heart 7.

As the distal end 14 of the delivery device 10b advances into the aortic arch 5, the user may operate the steering actuator 42 to maneuver the steerable portion 40 of the sleeve 30b, for example, by rotating the steering actuator 42 about the rest of the sleeve. As the steering actuator 42 is rotated, a pull mechanism (not shown) of the steering actuator 42 may pull a pull-wire extending along one side of the sleeve 30b that pulls one side of the pull-ring and bends the steerable portion 40 of the sleeve 30b to more easily conform to the curved shape of the aortic arch 5. Alternatively, as mentioned above, the steerable portion 40 may passively curve around the aortic arch 5 as the distal end 14 is advanced towards the annulus 6.

Preferably, the sleeve 30b is initially positioned with the steerable portion 40 contacting the proximal end of the distal sheath 24 (e.g., as shown in FIG. 4A), so that the steerable portion can more effectively steer the distal sheath 24 around the aortic arch 5 during advancement of the device 10b through the vasculature. After the distal sheath 24 has reached the annulus 6, the sleeve 30b can be retracted proximally, preferably by about 2" or the length of the distal sheath 24 (e.g., to the location shown in FIG. 3B), so that the distal sheath 24 will have sufficient room to retract and fully expose the compartment 23 to deploy a self-expandable heart valve contained therein.

In some embodiments (not shown), the pull-ring and the steerable portion 40 may not be located at the distal end of the sleeve 30b. In such embodiments, the steerable portion 40 and the pull-ring may be located in a middle portion of the sleeve 30b, and there may be more rigid portions of the sleeve located on both ends of the steerable portion 40.

Additionally, the steering actuator may be operated by techniques other than rotation, including pulling on the steering actuator, pressing a button on the steering actuator, or any other conventional actuation technique.

Referring now to FIG. 4A, another embodiment of a delivery device 10c is shown. The delivery device 10c is substantially the same as the delivery device 10b shown in FIGS. 3A and 3B, except that the steerable portion 40c of the sleeve 30c is located more distally along the outer shaft (not visible in FIGS. 4A and 4B), and the steering actuator 42c extends at an angle from the hub 32c of the sleeve 30c. The delivery device 10c has a proximal end (not shown), a distal end 14, and a catheter assembly 16c extending from the proximal end to the distal end 14.

The catheter assembly 16c includes an inner shaft (not shown, but located inside the sleeve) extending from a hub (not shown) to the distal end 14, and an outer shaft (not shown, but located inside the sleeve) assembled over the inner shaft for sliding movement relative thereto. At the distal end of the outer shaft, the catheter assembly 16c includes a valve compartment 23 for holding a prosthetic heart valve in a collapsed condition around the inner shaft for delivery into a patient. A distal sheath 24 encloses the compartment 23 and is connected to the distal end of the outer shaft so that sliding movement of the outer shaft along the inner shaft results in a corresponding movement of the distal sheath 24 relative to the compartment 23 for deployment of the heart valve. At its proximal end, the outer shaft includes a hemostasis valve (not shown). A long and steerable sleeve 30c having a hub 32c at its proximal end is assembled over the outer shaft distally of the hemostasis valve. Similar to the sleeve 30a shown in FIGS. 2A and 2B and the sleeve 30b shown in FIGS. 3A and 3B, the sleeve 30c preferably has a length that is about 2" shorter than the distance between the hemostasis valve and the proximal end of the distal sheath 24. In example embodiments, the sleeve 30c may have a length between about 24" and about 42".

The sleeve 30c includes a steerable portion or distal section 40c located at the distal end of the sleeve and abutting the proximal end of the distal sheath 24, a proximal portion 41c, a steering actuator 42c extending from the catheter assembly 16c near the proximal portion of the sleeve, a pull-ring (not shown) embedded in a distal end 44c of the steerable portion 40c, and one or more pull-wires (not shown) extending longitudinally along a side wall of the sleeve and coupled at one end to the pull-ring and at the other end to a pull mechanism of the steering actuator 42c.

As described above with reference to the steering actuator 42 shown in FIGS. 3A and 3B, a user may actuate the steering actuator 42c to maneuver the steerable portion 40c of the sleeve 30c through the curved shape of the aortic arch, for example, by rotating the steering actuator 42c about its longitudinal axis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for an implantable medical device, the delivery device comprising:
   an inner shaft extending in a longitudinal direction, the inner shaft defining a compartment adapted to receive the medical device in an assembled condition;
   an outer shaft surrounding at least a longitudinal portion of the inner shaft, the outer shaft being slidable relative to the inner shaft in the longitudinal direction, the outer shaft including a hemostasis valve at a proximal end thereof having an adjustable sealing member and a side port for flushing the space between the outer shaft and the inner shaft;
   a distal sheath operatively attached to the outer shaft and surrounding a longitudinal portion of the inner shaft, the distal sheath having an outer diameter and being slidable in the longitudinal direction between a first position enclosing the compartment and a second position exposing the compartment for deployment of the medical device; and a sleeve surrounding a longitudinal portion of the outer shaft and extending from a location close to the hemostasis valve to a location close to the distal sheath but sufficiently spaced from the distal sheath that the distal sheath is configured to be fully retracted off of the compartment without contacting the sleeve, the hemostasis valve being disposed proximal to a proximal end of the sleeve, the sleeve having an inner diameter less than the outer diameter of the distal sheath, the sleeve being slidably assembled over the outer shaft distally of the hemostasis valve and proximally of the distal sheath, the sleeve configured to have a range of motion during delivery of the implantable medical device into a patient, the range of motion limited proximally by the hemostasis valve and limited distally by the distal sheath, the sleeve configured to be slidable relative to the outer shaft, the inner shaft, and the hemostasis valve during delivery of the implantable medical device into a patient wherein the sleeve includes a hub having an outer diameter sized and configured to be greater than an inner diameter of an interior lumen of an introducer comprising an introducer valve, so that the hub is configured to prevent the sleeve from fully passing into the introducer and from fully passing through the introducer valve, wherein the inner diameter of the sleeve is closely matched with an outer diameter of the outer shaft, such that a gap between the sleeve and the outer shaft is sufficiently small that the gap is configured to prevent significant flow of blood into the gap.

2. The delivery device of claim 1, wherein the sleeve and the outer shaft define an average clearance therebetween of between about 0.001 inches and about 0.002 inches.

3. The delivery device of claim 1, further comprising a handle coupled to the inner and outer shafts and adapted to slide the outer shaft in the longitudinal direction relative to the inner shaft.

4. The delivery device of claim 1, wherein the sleeve is configured to be non-removable from the outer shaft.

5. The delivery device of claim 1, wherein the sleeve is splittable in the longitudinal direction for removal from the outer shaft.

6. The delivery device of claim 1, wherein the sleeve has an outer surface that tapers in the longitudinal direction from a relatively large proximal diameter to a relatively small distal diameter.

7. The delivery device of claim 1, wherein the sleeve includes a distal steerable portion and a proximal portion, the steerable portion being more flexible than the proximal portion.

8. The delivery device of claim 7, further comprising a steering actuator coupled to the sleeve, wherein operation of the steering actuator bends the steerable portion of the sleeve.

9. The delivery device of claim 8, further comprising a pull-wire extending in the longitudinal direction from the steering actuator to a distal end of the steerable portion, whereby operation of the steering actuator causes the pull-wire to pull on the distal end of the steerable portion.

10. A system for implantable medical device delivery, the system comprising:

an introducer having an interior lumen and an introducer valve located in the interior lumen; and a delivery device including
an inner shaft extending in a longitudinal direction, the inner shaft defining a compartment adapted to receive the medical device in an assembled condition;
an outer shaft surrounding at least a longitudinal portion of the inner shaft, the outer shaft being slidable relative to the inner shaft in the longitudinal direction, the outer shaft including a hemostasis valve at a proximal end thereof having an adjustable sealing member and a side port for flushing the space between the outer shaft and the inner shaft;
a distal sheath operatively attached to the outer shaft and surrounding a longitudinal portion of the inner shaft, the distal sheath being slidable in the longitudinal direction between a first position enclosing the compartment and a second position exposing the compartment for deployment of the medical device; and
a sleeve surrounding a longitudinal portion of the outer shaft and extending from a location close to the hemostasis valve to a location close to the distal sheath but sufficiently spaced from the distal sheath that the distal sheath is configured to be fully retracted off of the compartment without contacting the sleeve, the hemostasis valve being disposed proximal to a proximal end of the sleeve, the sleeve being slidably assembled over the outer shaft distally of the hemostasis valve and proximally of the distal sheath, the sleeve configured to have a range of motion during delivery of the implantable medical device into a patient, the range of motion limited proximally by the hemostasis valve and limited distally by the distal sheath, the sleeve configured to be slidable relative to the outer shaft, the inner shaft, and the hemostasis valve during delivery of the implantable medical device into a patient, wherein an inner diameter of the sleeve is closely matched with an outer diameter of the outer shaft, such that a gap between the sleeve and the outer shaft is sufficiently small that the gap is configured to prevent significant flow of blood into the gap wherein the sleeve includes a hub having an outer diameter that is greater than an inner diameter of the interior lumen of the introducer, so that the hub is configured to prevent the sleeve from fully passing into the introducer and from fully passing through the introducer valve;
the delivery device being assembled in the introducer so that the sleeve is positioned in the interior lumen of the introducer and extends through the introducer valve.

11. The system of claim 10, wherein the sleeve and the outer shaft define an average clearance therebetween of between about 0.001 inches and about 0.002 inches.

12. The system of claim 10, wherein the delivery device includes a handle coupled to the inner and outer shafts and adapted to slide the outer shaft in the longitudinal direction relative to the inner shaft.

13. The system of claim 10, wherein the sleeve is configured to be non-removable from the outer shaft.

14. The system of claim 10, wherein the sleeve is splittable in the longitudinal direction for removal from the outer shaft.

15. The system of claim 10, wherein the sleeve has an outer surface that tapers in the longitudinal direction from a relatively large proximal diameter to a relatively small distal diameter.

16. The system of claim 10, wherein the sleeve includes a distal steerable portion and a proximal portion, the steerable portion being more flexible than the proximal portion.

17. The system of claim 16, wherein the delivery device includes a steering actuator coupled to the sleeve, whereby operation of the steering actuator bends the steerable portion of the sleeve.

18. The system of claim 17, wherein the delivery device includes a pull-wire extending in the longitudinal direction from the steering actuator to a distal end of the steerable portion, whereby operation of the steering actuator causes the pull-wire to pull on the distal end of the steerable portion.

19. A method of delivering an implantable medical device, comprising:

providing a delivery device including an inner shaft extending in a longitudinal direction, the inner shaft defining a compartment adapted to receive the medical device in an assembled condition, an outer shaft surrounding at least a longitudinal portion of the inner shaft, the outer shaft being slidable relative to the inner shaft in the longitudinal direction, the outer shaft including a hemostasis valve at a proximal end thereof having an adjustable sealing member and a side port for flushing the space between the outer shaft and the inner shaft, a distal sheath operatively attached to the outer shaft and surrounding a longitudinal portion of the inner shaft, the distal sheath being slidable in the longitudinal direction between a first position enclosing the compartment and a second position exposing the compartment for deployment of the medical device, and a sleeve surrounding a longitudinal portion of the outer shaft and extending from a location close to the hemostasis valve to a location close to the distal sheath but sufficiently spaced from the distal sheath that the distal sheath is configured to be fully retracted off of the compartment without contacting the sleeve, the hemostasis valve being disposed proximal to a proximal end of the sleeve, the sleeve being slidably assembled over the outer shaft distally of the hemostasis valve and proximally of the distal sheath, the sleeve configured to have a range of motion during delivery of the implantable medical device into a patient, the range of motion limited proximally by the hemostasis valve and limited distally by the distal sheath, the sleeve configured to be slidable relative to the outer shaft, the inner shaft, and the hemostasis valve during delivery of the implantable medical device into a patient, wherein an inner diameter of the sleeve is closely matched with an outer diameter of the outer shaft, such that a gap between the sleeve and the outer shaft is sufficiently small that the gap is configured to prevent significant flow of blood into the gap;

mounting the medical device in the compartment with the distal sheath in the first position;

providing an introducer in a tract extending from an opening in a blood vessel of the patient and through tissue overlying the opening, the introducer having an interior lumen and an introducer valve located in the interior lumen wherein the sleeve includes a hub having an outer diameter that is greater than an inner diameter of the interior lumen of the introducer, so that the hub is configured to prevent the sleeve from fully passing into the introducer and from fully passing through the introducer valve;

inserting the distal sheath of the delivery device into the patient through the introducer to position the medical device at a target location;

positioning the sleeve in the introducer with the hemostasis valve disposed proximally of the introducer and the distal sheath disposed distally of the introducer, the introducer valve creating a substantially leak-proof seal against an outer surface of the sleeve;

advancing the distal sheath of the delivery device into the aortic arch of the patient; and deploying the medical device by withdrawing a proximal portion of the outer shaft out of the introducer, thereby sliding the distal sheath into the second position.

20. The method of claim 19, wherein the medical device is a prosthetic heart valve, and the target location is the descending aorta.

21. The method of claim 19, further comprising removing the sleeve from the introducer by splitting it along a predetermined longitudinal score and peeling the sleeve away from the outer shaft.

22. The method of claim 19, wherein the sleeve includes a distal steerable portion and a proximal portion, the steerable portion being more flexible than the proximal portion, and the delivery device includes a steering actuator coupled to the sleeve, the method further comprising:

operating the steering actuator to bend the steerable portion of the sleeve.

23. The method of claim 22, wherein the delivery device includes a pull-wire extending in the longitudinal direction from the steering actuator to a distal end of the steerable portion, the method further comprising:

operating the steering actuator to cause the pull-wire to pull on the distal end of the steerable portion, thereby bending the deflectable portion.

* * * * *